US010912725B2

(12) United States Patent
Scala et al.

(10) Patent No.: US 10,912,725 B2
(45) Date of Patent: Feb. 9, 2021

(54) CLEANSING COMPOSITION

(71) Applicant: Colgate-Palmolive Company, New York, NY (US)

(72) Inventors: Diana Scala, Hillsborough, NJ (US); Patricia Hall-Puzio, Succasunna, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/456,633

(22) Filed: Mar. 13, 2017

(65) Prior Publication Data
US 2017/0181944 A1 Jun. 29, 2017

Related U.S. Application Data

(62) Division of application No. 13/992,749, filed as application No. PCT/US2010/059612 on Dec. 9, 2010, now Pat. No. 9,622,943.

(51) Int. Cl.
| | |
|---|---|
| A61K 8/36 | (2006.01) |
| A61K 8/25 | (2006.01) |
| A61Q 19/10 | (2006.01) |
| C11D 3/12 | (2006.01) |
| C11D 3/37 | (2006.01) |
| C11D 17/08 | (2006.01) |
| A61K 8/26 | (2006.01) |
| A61K 8/34 | (2006.01) |
| A61K 8/41 | (2006.01) |
| A61K 8/91 | (2006.01) |
| A61K 8/02 | (2006.01) |
| A61K 8/19 | (2006.01) |

(52) U.S. Cl.
CPC ............... *A61K 8/361* (2013.01); *A61K 8/02* (2013.01); *A61K 8/19* (2013.01); *A61K 8/25* (2013.01); *A61K 8/26* (2013.01); *A61K 8/342* (2013.01); *A61K 8/41* (2013.01); *A61K 8/91* (2013.01); *A61Q 19/10* (2013.01); *C11D 3/1266* (2013.01); *C11D 3/3765* (2013.01); *C11D 17/08* (2013.01); *A61K 2800/48* (2013.01)

(58) Field of Classification Search
CPC ... A61K 8/02; A61K 8/19; A61K 8/25; A61K 8/26; A61K 8/342; A61K 8/361; A61K 8/41; A61K 8/91; A61K 2800/48; A61Q 19/10; C11D 17/08; C11D 3/1266; C11D 3/3765
See application file for complete search history.

(56) References Cited

U.S. PATENT DOCUMENTS

| | | | |
|---|---|---|---|
| 3,520,818 A | 7/1970 | Cambre | |
| 3,929,678 A | 12/1975 | Laughlin et al. | |
| 4,472,287 A | 9/1984 | Ramachandran et al. | |
| 4,673,525 A | 6/1987 | Small et al. | 510/151 |
| 4,678,593 A | 7/1987 | Ridley | |
| 4,800,076 A | 1/1989 | Bhat et al. | |
| 4,975,218 A | 12/1990 | Rosser | |
| 5,846,549 A | 12/1998 | Beauquey et al. | |
| 5,851,978 A * | 12/1998 | Shana'a | A61K 8/26 510/417 |
| 5,866,040 A | 2/1999 | Nakama et al. | |
| 6,136,765 A | 10/2000 | Glenn, Jr. et al. | |
| 6,534,687 B2 | 3/2003 | Schultz et al. | |
| 6,537,953 B2 | 3/2003 | Schultz et al. | |
| 6,537,954 B2 | 3/2003 | Schultz et al. | |
| 6,541,433 B2 | 4/2003 | Schultz et al. | |
| 6,589,923 B2 | 7/2003 | Lenuck et al. | |
| 6,949,493 B1 | 9/2005 | Zhang et al. | |
| 2005/0187129 A1 | 8/2005 | Chakrabarty et al. | |
| 2006/0239955 A1 | 10/2006 | Chandar et al. | |
| 2008/0125340 A1 | 5/2008 | Dail | |
| 2008/0153728 A1 | 6/2008 | Dail et al. | |
| 2008/0242573 A1* | 10/2008 | Wei | A61K 8/044 510/159 |
| 2010/0119562 A1 | 5/2010 | Hilliard, Jr. et al. | |

FOREIGN PATENT DOCUMENTS

| | | |
|---|---|---|
| EP | 0661047 | 7/1995 |
| EP | 0861317 | 1/2000 |
| EP | 1422288 | 5/2004 |
| GB | 2143841 | 2/1985 |
| RU | 2290920 | 1/2007 |
| WO | 2003/097006 | 11/2003 |
| WO | WO 03/097006 | 11/2003 |
| WO | 2004/080431 | 9/2004 |
| WO | WO 05/094779 | 10/2005 |
| WO | WO 06/097238 | 9/2006 |
| WO | 2007/103968 | 9/2007 |
| WO | WO 08/098717 | 8/2008 |
| WO | 2008/116147 | 9/2008 |
| WO | WO 10/057850 | 5/2010 |

(Continued)

OTHER PUBLICATIONS

DOW Aculyn April (Year: 2005).*
Dow Chemical Company, 2010, "Aculyn 88 Product Detail".
International Search Report and Written Opinion in International Application No. PCT/US10/059612, dated Aug. 26, 2011.
Rohm and Haas, 2005, "Aculyn™ 88 Rheology Modifier".
Rockwood Specialties Group, Inc., "Laponite XL21 Product Data Sheet," retrieved from internet 2013.
Rockwood Specialties Group, Inc., "Laponite XLG Product Bulletin," retrieved from internet 2013.
Written Opinion in International Application No. PCT/US10/059612, dated Jan. 3, 2013.

(Continued)

Primary Examiner — Matthew P Coughlin
Assistant Examiner — Thurman Wheeler

(57) ABSTRACT

A liquid cleansing composition comprising water in an amount sufficient to form a liquid composition, a fatty acid soap, a structuring agent, and talc. The cleansing composition has a creamy texture and provides good skinfeel properties.

15 Claims, No Drawings

(56) References Cited

FOREIGN PATENT DOCUMENTS

WO    2010/083069    7/2010
WO    WO 10/101534  9/2010

OTHER PUBLICATIONS

Eu Yan Sang, 2010, "Antibacterial Hand Wash Lotion," Database Mintel GNPD AN: 1275250.
Grocery Holdings, 2010, "Gentle & Effective Cleansing Lotion," Database Mintel GNPD AN: 1348485.
Johnson & Johnson, 2010, "Neutrogena Deep Clean," Database Mintel GNPD AN: 1232176.

* cited by examiner

CLEANSING COMPOSITION

FIELD OF THE INVENTION

Disclosed are cleansing compositions.

BACKGROUND OF THE INVENTION

Soaps are made from neutralized fatty acids. Typically, they are provided in a solid form, such as a soap bar. Soaps have also been made into liquid forms, and they have been structured. The problem is that the structured liquid soap provides a rheology that may not be appealing to consumers.

It would be desirable to provide a structured, liquid soap composition that has a creamy texture that could be more appealing to consumers.

BRIEF SUMMARY OF THE INVENTION

A liquid cleansing composition comprising water in an amount sufficient to form a liquid composition, a fatty acid soap, a structuring agent, and talc.

Also, a method comprising applying the composition to skin and cleansing the skin, and optionally, rinsing the skin.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

Disclosed is a liquid cleansing composition comprising water in an amount sufficient to form a liquid composition, a fatty acid soap, a structuring agent, and talc. The addition of talc provides a modification to the rheological properties of a liquid soap composition to provide a creamy texture.

The fatty acid soap can be any of the neutralized fatty acids. Typical fatty acids used for soaps include, myristic acid, lauric acid, palmitic acid, stearic acids, and other fatty acids. Sources of fatty acids include coconut oil, palm oil, palm kernel oil, tallow, avocado, canola, corn, cottonseed, olive, hi-oleic sunflower, mid-oleic sunflower, sunflower, palm stearin, palm kernel olein, safflower, and babassu oils. The fatty acids can be neutralized with any base to form a soap. Typical bases include, but are not limited to, sodium hydroxide, potassium hydroxide, and triethanolamine. In certain embodiments, the fatty acid soap is present in the composition in an amount up to 30 weight %. In other embodiments, the amount is 10 to 30 weight %, 10 to 20 weight %, or at least 11, 12, 13, 14, 15, 16, 17, 18, 19, or 20 up to 30 weight %.

In certain embodiments, the fatty acid soap is formed from fatty acids neutralized by two or more bases. In certain embodiments, the bases are sodium hydroxide and triethanolamine. In certain embodiments, the molar ratio of sodium hydroxide and triethanolamine is about 1:1. In certain embodiments, the fatty acids are stearic acid and Laurie acid. In certain embodiments, the amount of stearic acid based on a total weight of starting fatty acids is 60 weight %, and the amount of lauric acid based on a total weight of starting fatty acids is 40 weight %.

The soap can be made in situ in the composition by mixing fatty acids with the neutralizing agent. In certain embodiments, the molar amount of fatty acids is greater than the molar amount of neutralizing agent such that fatty acid remains in the composition. In certain embodiments, the total amount of soap includes the neutralized fatty acids and free fatty acids. In certain embodiments, the amount of free fatty acids is up to 20 weight % of the total amount of soap in the composition.

Water is present in the composition in an amount that is sufficient to form a liquid composition. In certain embodiments, the amount of water is at least 65 weight %, or 65 to 90 weight %. In other embodiments the amount of water is 75 to 85 weight %.

The structuring agent is any material that can increase viscosity or yield point in the composition. Examples of the structuring agent include, but are not limited to, clay, polymers, polymeric gums, polysaccharides, microfibrous cellulose, gellan gum, pectine, alginate, arabinogalactan, carageenan, xanthum gum, guar gum, rhamsan gum, furcellaran gum, and other natural gums. In certain embodiments, the amount of structuring agent is 0.1 to 2 weight %. In other embodiments, the amount is 0.5 to 1.1 weight %.

The clay can be any type of clay. Examples of clays include, but are not limited to, kaolin, kaolinite, dickite, halloysite, nacrite, smectite, montmorillonite, nontronite, illite, bentonite, attapulgite, palygorskite, sepiolite, hormite, pyrophyllite, chlorite, aluminosilicates, and synthetic layered clays. In certain embodiments, the clay can be Laponite™ XLG or XL21 synthetic layered silicate, which can be obtained from Southern Clay Products/Rockwood international. In certain embodiments, the amount of clay is 0.3 to 0.5 weight %.

A polymer structuring agent in one embodiment is a polyacrylate. Examples of polyacrylates are the Aculyn™ polymers from Dow/Rohm and Haas. In one embodiment, the structuring agent is Aculyn™ 88 acrylates/steareth-20 methacrylate crosspolymer, which is sold as a 29 weight % polymer in water composition. In one embodiment, the Aculyn™ 88 acrylates/steareth-20 methacrylate crosspolymer is present in an amount of 0.2 to 0.6 weight % (active weight).

Examples of other acrylates are manufactured by Noveon, such as CARBOPOL™ Aqua 30, Aqua SF1, and Aqua SF2. The CARBOPOL™ resins, also known as CARBOMER™, are hydrophilic high molecular weight, crosslinked acrylic acid polymers having an average equivalent weight of 76, and the general structure illustrated by the following formula has a molecular weight of about 1,250,000; CARBOPOL™ 940 with a molecular weight of approximately 4,000,000 and CARBOPOL™ 934 with a molecular weight of approximately 3,000,000. The CARBOPOL™ resins can be crosslinked with polyalkenyl polyether, e.g. about 1% of a polvalkyl ether of sucrose having an average of about 5,8 alkyl groups for each molecule of sucrose.

In certain embodiments, the structuring agent is a combination of clay, such as Laponite™ XLG and/or XL21 synthetic layered silicate, and Aculyn™ 88 acrylates/steareth-20 methacrylate crosspolymer.

Talc is included in the composition. In certain embodiments the amount of talc is up to 10 weight %. In certain embodiments, the amount is 4 to 6 weight %. The talc is in powder form. An example of talc is Steasilk™ 5CH from Luzenac.

In one embodiment, the cleansing composition comprises 75 to 85 weight % water, 10 to 20 weight % soap (preferably a triethanolamine and sodium soap), 4-6 weight % talc, 1 to 2 weight % (as supplied at about 29% active) Aculyn™ 88 acrylates/steareth-20 methacrylate crosspolymer, and 0.3 to 0.5 weight % clay.

The composition can provide a creamy texture, provide good lather and skin feel can be easily rinsed from the skin.

In other embodiments, the composition may include any of following materials in any desired amount to achieve a desired effect in the composition (amounts that can be used in some embodiments are provided): one or more alkaline salts, for example, sodium chloride, sodium sulfate, sodium carbonate, sodium bicarbonate and/or their equivalents (0 to 5% by weight); foaming agents, for example decyl glucoside, and/or their equivalents (0 to 3% by weight); glyceryl esters and derivatives, for example glycol distearate, and/or their equivalents (0 to 3%; by weight); sequestrants, for example, tetrasodium EDTA, and/or their equivalents (0 to 2% by weight); biocides, for example, Triclosan (2,4,4'-trichloro-2'-hydroxydiphenyl ether), DMDM hydantoin, formaldehyde and/or imidazolidinyl urea, and/or their equivalents (0 to 2% by weight); organic acids, for example, citric acid and/or formic acid and/or their equivalents (0 to 2% by weight); viscosity modifiers (0 to 2% by weight); fragrances and/or perfumes (0 to 5% by weight); preservatives, for example, phenoxyethanol, formaldehyde solution, parabens, pentanediol or sorbic acid (0 to 2% by weight); pearlizing agents, for example, glycol distearic esters, such as ethylene glycol distearate, but also fatty acid monoglycol esters (0 to 3% by weight); and dyes and pigments that are approved and suitable for cosmetic purposes.

Also, a method comprising applying the composition to skin and cleansing the skin, and optionally, rinsing the skin.

SPECIFIC EMBODIMENTS

The invention is further described in the following examples. The examples are merely illustrative and do not in any way limit the scope of the invention as described and claimed.

The following comparative and inventive compositions are prepared as follows. The amounts listed are the as supplied weights of the materials.

Part 1:

Add the formula amount of deionized water to a suitable container. Mix with a propeller mixer at around 300 rpm. Add clay, if present in the formulation, and mix for about 10 minutes. Start heating the solution up to about 80° C.

Part 2:

Weigh the appropriate amount of the fatty acids in a separate container. Heat until it is fully melted and mix gently.

Part 3:

When the clay (if applicable) is fully dispersed in Part 1, slowly add the base (TEA, NaOH or KOH). After about 5 minutes of mixing, add Part 2. Shut off heat and continue mixing for about 5 minutes. Add talc (if applicable) and continue mixing for about 5 minutes. Add Aculyn™ 88 (if applicable) and mix for about 3 minutes. Let stand to cool to room temp.

| Weight % | A | B | C | D | E | F | G | H |
|---|---|---|---|---|---|---|---|---|
| Deionized water | 83.63 | 81.89 | 85.00 | 85.40 | 85.66 | 77.37 | 79.60 | 75.54 |
| Laponite ™ XL21 Clay | 0.49 | 0.51 | 0.50 | 0.30 | — | — | — | 0.47 |
| Triethanolamine | 9.84 | 9.99 | — | — | — | 2.90 | 2.98 | 2.83 |
| 50% NaOH | — | — | 3.50 | 1.81 | 1.81 | 2.13 | 2.98 | 2.08 |
| 50% KOH | — | — | — | 2.44 | 2.45 | — | — | — |
| Stearic acid | — | — | — | — | — | 7.66 | 7.88 | 7.48 |
| Palmitic acid | 3.02 | 3.00 | 6.00 | 6.03 | 6.05 | — | — | — |
| Myristic acid | 3.02 | 3.00 | — | — | — | — | — | — |
| Lauric acid | — | — | 4.00 | 4.02 | 4.03 | 5.11 | 5.25 | 4.99 |
| talc | — | — | — | — | — | 4.84 | — | 4.72 |
| Aculyn ™ 88 Acrylates/Steareth-20 Methacrylate Crosspolymer (29% active) | — | 1.62 | 1.00 | — | — | — | 1.30 | 1.89 |
| Total | 100 | 100 | 100 | 100 | 100 | 100 | 100 | 100 |
| | liquid; not gel | clear gel | solid | solid | liquid | thick white fluid | thick clear gel | viscous white opaque gel |
| | | soap rinses well; smooth skin afterfeel may be thicker | difficult to lather | feels harder than D good lather | | | good lather | talc can be better dispersed good lather, nice skin afterfeel good rinsability |

Formulations A&B demonstrate that Aculyn™ 88 structurant creates a mixture with a gel consistency. Formulation C demonstrates that the ease of generating lather increases with increased soap solubility (mixture of sodium and potassium soap (more soluble) vs. sodium soap alone). Additionally, the use of about 10% sodium soap produces a semi-hard solid composition. Formulations D&E perform similarly except that Laponite™ XL21 clay appears to create a harder formulation than the Laponite™ XLG clay. Formulation D & E demonstrate that a structurant is needed to structure the formulation. Formulation F demonstrates that the formula with talc, but without an auxiliary structurant produces a thick fluid but does not produce a creamy structure. Formulation I produces the creamy composition especially when it is mixed using a high shear mixer (Silverson @2000 rpm for about 30 sec, to 1 min).

Prior to Formulation the following was made: (Pre-F) 85 g deionized water, 0.5 g Laponite™ XL21 clay, 3 g YEA, 6 g stearic acid, and 4 g lauric acid. This created a non-lathering thick gel due to incomplete neutralization of the fatty acid. This was improved by adding additional base (5 drops of 50% NaOH) while mixing, resulting in sodium soap formation. This version created better lather attributes. To thicken the Pre-G formula, 50 mls of the mixture was added to a new beaker and 0.97 g of Aculyn™ 88 structurant was added. This thickened the formulation, and it produced a nice skin feel during and after washing. Talc (4.5 g) was added to the formulation and mixed with a spatula resulting in a creamy texture. It produced a nice skin feel; however, it exhibited a white talc residue on the skin. Therefore, subsequent formulations were made with lower amounts of talc to reduce the white residue.

Formula H was modified to reduce soap content and increase water to improve cost effectiveness. See Formula F below.

| | |
|---|---|
| Deionized water | 84.15 |
| Laponite XL21 clay | 0.38 |
| Triethanolamine | 0.94 |
| 50% NaOH | 1.32 |
| Stearic acid | 4.53 |
| Lauric acid | 3.02 |
| Talc | 4.72 |
| Aculyn™ 88 Acrylates/Steareth-20 Methacrylate Crosspolymer (29% active) | 0.94 |
| Total | 100 |

Formula I produced a nice creamy texture with good lather and skin feel.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

What is claimed is:

1. A liquid cleansing composition consisting of:
   water in a sufficient amount to form a liquid composition;
   fatty acid soap; and
   a structuring agent which is at least one of clay and acrylates/steareth-20 methacrylate crosspolymer.

2. The composition of claim 1, wherein the fatty acid soap is present in an amount of 10 to 30 weight %.

3. The composition of claim 1, wherein the structuring agent is present in an amount of 0.1 to 2 weight %.

4. The composition of claim 1, wherein the fatty acid soap is a neutralized stearic acid and lauric acid.

5. The composition claim 1, wherein the clay is present in an amount of 0.3 to 0.5 weight %, based on a total weight of the composition.

6. The composition of claim 1, wherein the fatty acid soap is neutralized stearic acid and lauric acid with free fatty acid.

7. The composition of claim 1, wherein the water is present in an amount of from 75 weight % to 90 weight %, based on the total weight of the composition.

8. A liquid cleansing composition consisting of:
   water in a sufficient amount to form a liquid composition;
   fatty acid soap; and
   a structuring agent;
   wherein the fatty acid soap is formed from Stearic acid, Palmitic acid, Myristic acid, and/or Lauric acid neutralized with Triethanolamine, NaOH and/or KOH.

9. The liquid cleansing composition of claim 8, wherein the fatty acids is stearic acid and lauric acid.

10. The liquid cleansing composition of claim 9, wherein the stearic acid is present in an amount of about 60% and the lauric acid is present in an amount of about 40%, based on a total weight of the fatty acids before neutralization.

11. The liquid cleansing composition of claim 9, wherein the stearic acid is present in an amount of from 6 weight % to 8 weight %, based on the total weight of the composition.

12. The liquid cleansing composition of claim 9, wherein the stearic acid is present in an amount of from 4 weight % to 5 weight %, based on the total weight of the composition.

13. The liquid cleansing composition of claim 9, wherein the lauric acid is present in an amount of from 4 weight % to 6 weight %, based on the total weight of the composition.

14. The liquid cleansing composition of claim 9, wherein the lauric acid is present in an amount of from 2.5 weight % to 3.5 weight %, based on the total weight of the composition.

15. The liquid cleansing composition of claim 8, wherein the sodium hydroxide is present in an amount of from 0.6 weight % to 0.7 weight %, based on the total weight of the composition.

* * * * *